(12) United States Patent
Herbert

(10) Patent No.: US 6,605,646 B2
(45) Date of Patent: Aug. 12, 2003

(54) VITAMIN SUPPLEMENT COMPOSITION

(75) Inventor: Victor D. Herbert, New York, NY (US)

(73) Assignee: Upsher-Smith Laboratories, Inc., Minneapolis, MN (US)

( * ) Notice: Subject to any disclaimer, the term of this patent is extended or adjusted under 35 U.S.C. 154(b) by 0 days.

(21) Appl. No.: 10/215,421

(22) Filed: Aug. 9, 2002

(65) Prior Publication Data

US 2002/0193341 A1 Dec. 19, 2002

Related U.S. Application Data

(60) Continuation of application No. 09/862,693, filed on May 22, 2001, now abandoned, which is a continuation of application No. 09/549,756, filed on Apr. 14, 2000, now Pat. No. 6,265,391, which is a continuation-in-part of application No. 09/291,372, filed on Apr. 14, 1999, now abandoned, which is a division of application No. 08/544,330, filed on Oct. 17, 1995, now Pat. No. 5,932,624.

(51) Int. Cl.$^7$ ................................................. A61K 3/00
(52) U.S. Cl. ...................... 514/904; 536/26.4; 544/250; 546/301
(58) Field of Search .................. 514/904; 536/26.4; 544/250; 246/301

(56) References Cited

U.S. PATENT DOCUMENTS

| | | | |
|---|---|---|---|
| 2,748,054 A | 5/1956 | Jurist | 424/181 |
| 4,053,593 A | 10/1977 | Frumoff | 424/181 |
| 4,940,658 A | 7/1990 | Allen et al. | 435/4 |
| 4,945,083 A | 7/1990 | Jansen, Jr. | 514/52 |
| 5,039,668 A | 8/1991 | Colina | 435/34 |
| 5,064,829 A | 11/1991 | Izuhara et al. | 436/126 |
| 5,135,851 A | 8/1992 | Kajander | 424/439 |
| 5,374,560 A | 12/1994 | Allen et al. | 514/562 |
| 5,494,678 A | 2/1996 | Paradissis et al. | 514/52 |
| 5,545,670 A | 8/1996 | Bissbort et al. | 514/52 |
| 5,563,126 A | 10/1996 | Allen et al. | 424/682 |
| 5,795,873 A | 8/1998 | Allen | 514/52 |
| 5,849,338 A | 12/1998 | Richardson et al. | 424/682 |
| 5,932,624 A | 8/1999 | Herbert | |
| 5,997,915 A | 12/1999 | Bailey et al. | 514/907 |
| 6,043,259 A | 3/2000 | Dhalla et al. | 514/345 |

FOREIGN PATENT DOCUMENTS

| | | |
|---|---|---|
| DE | 4326675 | 2/1995 |
| DE | 43 26 698 | 3/1995 |
| DE | 4326698 | 3/1995 |
| EP | 0595005 | 5/1994 |
| EP | 0595006 | 5/1994 |
| JP | 53-123337 | 10/1978 |
| JP | 55049313 A2 | 4/1980 |
| JP | 3007230 A2 | 1/1991 |
| JP | 6192105 A2 | 7/1994 |
| WO | WO93/15738 | 8/1993 |
| WO | 95/15750 | 6/1995 |
| WO | WO00/56295 | 9/2000 |
| ZA | 936723 | 9/1993 |

OTHER PUBLICATIONS

Refsum, H. et al., "Acute and Long–Term Effects of High–Dose Methotrexate Treatment on Homocysteine in Plasma and Urine," *Cancer Research*, vol. 46(10), pp. 5385–5391. Oct. 1986.

"Drug Facts and Comparisons," edited by B.R. Olin et al., Wolters Fluwer Co., pp. 60–63, Feb. 1995.

Wighton et al., "Brain damage in infancy and dietary vitamin B12 deficiency," *Medical Journal of Australia*, vol. 2, No. 1, pp. 1–3, Abstract Only, Jul. 1979.

Malinow, "Plasma Homocyst(e)ine and Arterial Occlusive Diseases: A Mini–Review," *Clinical Chemistry*, 41(1), 173–176, Jan. 1995.

Ueland et al., "Total Homocysteine in Plasma or Serum: Methods and Clinical Applications," *Clinical Chemistry*, 19(9), 1764–1779, Sep. 1993.

Selhub et al., "Vitamin Status and Intake as Primary Determinants of Homocysteinemia in an Elderly Population," *Journal American Medical Association*, 270(22), 2693–2698, Dec. 8, 1993.

Huff et all, Physician' Desk Reference for Nonprescription Drugs. New Jersey: Medical Economics Company, Inc., 1985, $6^{th}$ edition, p. 507.

Mason et al., "The Effects of Vitamins $B_{12}$, $B_6$, and Folate on Blood Homocysteine Levels," Beyond Deficiency, New View on the Function and Health Effect of Vitamins, *Annals of the New York Academy of Sciences*, vol. 669, pp. 197–204, 1992.

Enstrom et al., "Mortality among health–conscious elderly Californians," *Proceedings of the National Academy of Sciences*, vol. 79, No. 19, pp. 6023–6027, Oct. 1982.

Parthasarathy et al., "The Role of Oxidized Low–Density Lipoproteins in the Pathogenesis of Atherosclerosis," *Annual Review of Medicine: Selected Topics in the Clinical Sciences*, vol. 43, pp. 219–225, 1992.

Stampfer et al., "A Prospective Study of Plasma Homocyst(e)ine and Risk of Myocaridal Infarction in US Physicians," *JAMA*, vol. 268, No. 7, pp. 877–881, Aug. 19, 1992.

Brattstrom et al., "Imparied homocysteine metabolism in early–onset cerebral and peripheral occlusive arterial disease, Effects of pyridoxine and folic acid treatment," *Atherosclerosis*, 81, pp. 51–60, 1990.

(List continued on next page.)

*Primary Examiner*—Zinna Northington Davis
(74) *Attorney, Agent, or Firm*—Kagan Binder, PLLC

(57) ABSTRACT

A vitamin $B_{12}$ supplement composition comprising vitamin $B_{12}$ with and/or without added folic acid that is essentially free of antioxidants, such as vitamin C, as well as iron is disclosed. Also disclosed are methods of using this vitamin composition to prevent brain and nervous system damage, such as peripheral nerve damage, as well as pernicious anemia, such as where such anemia is caused by a deficiency of vitamin $B_{12}$ deficiency.

7 Claims, No Drawings

OTHER PUBLICATIONS

Pechet, "Anemias and Other Red Cell Disorders," *Textbook of Primary Care Medicine, Second Edition*, pp. 722–734, 1996.

Stabler et al., "Clinical Spectrum and Diagnosis of Cobalamin Deficiency," *Blood*, vol. 76, No. 5, pp. 871–881, Sep. 1990.

"Homocysteine, Folic Acid, and the Prevention of Vascular Disease," *Nutrition Reviews*, vol. 47, No. 8, pp. 247–249, Aug. 1989.

Graham et al., "Plasma Homocysteine as a Risk Factor for Vascular Disease," *JAMA*, vol. 277, No. 22, pp. 1775–1781, Jun. 1997.

Ueland et al., "Plasma Homocysteine and Cardiovascular Disease," *Artherosclerotic Cardiovascular Disease, Hemostatsis, and Endothelial Functionp*, pp. 183–236, 1992.

Rosenblatt et al., "Vitamin $B_{12}$ Responsive Homocystinuria and Megaloblastic Anemia: Heterogeneity in Methylcobalamin Deficiency," *American Journal of Medical Genetics*, 26, pp. 377–383, 1987.

Wilcken, "Homocysteine in the plasma of renal transplant recipients: effects of cofactors for methionine metabolism," *Clinical Science*, 61, pp. 743–749, 1981.

Brattstrom et al., "Folic acid—an innocuous means to reduce plasma homocysteine," *Scand. J. Clin. Lab Invest.*, pp. 215–221, 1988.

Kang et al., "Hyperhomocyste(e)inemia as a Risk Factor for Occlusive Vascular Disease," *Annu. Rev. Nutr.*, 12, pp. 279–298, 1992.

Chasan–Taber et al., "A Prospective Study of Folate and Vitamin $B_6$ and Risk of Myocardial Infarction in US Physicians," *Journal of American College of Nutrition*, vol. 15, No. 2, pp. 136–143 (1996).

Ueland et al., "Plasma homocysteine, a risk factor for vascular disease: Plasma levels in health, disease, and drug therapy," *J. Lab Clin. Med.*, pp. 473–501, Nov. 1989.

Disorders of Red Cells, Megalolastic and Nonmegaloblastic Macrycytic Anemias, *Wintrobe's Clinical Hematology, Ninth Edition*, vol. 1, pp. 746–790, 1993.

Bland et al., Clinical Nutrition: A Functional Approach, The Institute for Functional Medicine, Gig Harbor, Washington, USA, pp. 5, 15, 113–125, 246–247, 1999.

Sauberlich et al, "Beyond Deficiency: New Views on the Function and Health Effects of Vitamins," *Annals of the New York Academy of Sciences*, vol. 669, pp. 4, 5, 23, 35–39, 1992.

V. Herbert, "Nutritional Requirements for Vitamin $B_{12}$ and Folic Acid," *The American Journal of Clinical Nutrition*, vol. 21, No. 7, pp. 743–752, Jul. 1968.

Herbert et al., "Destruction of vitamin $B_{12}$ by vitamin C," *The American Journal of Clinical Nutrition*, pp. 297–299, Mar. 1976.

Herbert, "Vitamin B–12 and folic acid supplementation," *The American Journal of Clinical Nutrition*, vol. 66, No. 6, pp. 1479–1480, Dec. 1997.

Herbert, "Drugs Effective in Megaloblastic Anemias, Vitamin $B_{12}$ and Folic Acid," *The Pharmacological Basis of Therapeutics, Fifth Edition*, pp. 1324–1349, 1975.

Herbert et al., "Destruction of Vitamin $B_{12}$ by Ascorbic Acid," *JAMA*, vol. 230, No. 2, pp. 241–242, Oct. 14, 1974.

Herbert, "The 1986 Herman Award Lecture. Nutrition science as a continually unfolding story: the folate and vitamin B–12 paradigm," *Am J Clin Nutr*, vol. 46, No. 3, pp. 387–402, 1987.

Herbert, "The Inhibition and Promotion of Cancers by Folic Acid, Vitamin $B_{12}$, and Their Antagonists," *ACS Symp. Ser.*, vol. 277, pp. 31–36, 1985.

Herbert "The Inhibition of Some cancers and the Promotion of Others by Folic Acid, Vitamin $B_{12}$, and Their Antagonists," *Birstol–Myers Nutr. Symp.*, vol. 2, pp. 273–287, 1983.

Herbert et al., "Multivitamin/Mineral Food Supplements Containing Vitamin $B_{12}$ May Also Contain Analogues of Vitamin $B_{12}$," *N. Engl. J. Med.*, vol. 307, No. 4, pp. 255–256, 1982.

V. Herbert, "Folic Acied and Vitamin B12," *Trends Haematol*, pp. 389–423, 1975.

V. Herbert, "To Prevent Vasculotoxicity From Hyperhomocysteinemia, Give Affected Children Vitamin $B_6$, Give Fertile Females Folate, and Give all > Age 50 Daily Oral 25 To 100 µg Vitamin $B_{12}$," *FASEB Journal*, vol. 13, No. 4, Abstract 208.4, p. A227, Mar. 1999.

V. Herbert, "0.4 Mg Folate Supplements are Desirable if They Contain 25 or more PLUS CODE 83 IS NOT DEFINEDg Vitamin $B_{12}$ and No Folate—and $B_{12}$ —Destroying Redox Agents Like Vitamin C and Iron," *FASEB Journal*, vol. 10, No. 3, Abstract 2679, p. A464, Mar. 1996.

Herbert et al., "Nutrition and Cancer –Vitamins C and E," *Total Nutrition*, p. 487 (1995).

Herbert, "Vitamin $B_{12}$," Letters to the Editor, *American Journal of Clinical Nutrition* vol. 34, No. 5, pp. 971–972 (May 1981).

Kondo et al., "Presence and Formation of Cobalamin Analogues in Multivitamin–Mineral Pills," *Journal of Clinical Investigation*, vol. 70, No. 4, pp. 889–898 (Oct. 1982).

Herbert Editorial, "Vitamin C Supplements and Disease–Counterpoint," appearing in *Journal of the American College of Clinical Nutrition*, vol. 14, No. 2, pp. 112–113 (1995).

Herbert, "Effects of Megadoses of Vitamin C on Vitamin $B_{12}$," *Present Knowledge in Nutrition*, ($5^{th}$ Ed), pp. 350–351 (1984).

Herbert et al., "Vitamin C–Driven Free Radical Generation from Iron$^{1.2}$," *The Journal of Nutrition*, vol. 126, Supplement 4, pp. 1213S–1220S (1996).

Herbert, V., "Vitamin B–12," *Present Knowledge in Nutrition* ($7^{th}$ Edition), Washington DC, ILSI Press, pp. 191–205 (1996).

Shaw et al., "Effect of Ethanol–Generated Free Radicals on Gastric Intrinsic Factor and Gluthatione," *Alcohol*, vol. 7, pp. 153–157 (1990).

Jacques et al., "The Effect of Folic Acid Fortification on Plasma Folate and Total Homocysteine Concentrations," *New England J. Medicine*, vol. 340, pp. 1449–1454 (1999).

Flynn et al., "Atherogenesis and the Homocysteine–Folate-Cobalamin Triad: Do We Need Standardized Analyses?" *J. Am. Coll. Nutr.*, vol. 16, No. 3, pp. 258–267 (1997).

Miller et al., "Oral Vitamin B12 Supplementation Decreases Homocysteine in Healthy Elderly People with Suboptimal Vitamin B12 Status," FASEB J., 13:A936, 690.1, (1997).

VITAMIN SUPPLEMENT COMPOSITION

This application is a continuation of Ser. No. 09/862,693 filed May 22, 2001, abandoned, which a continuation of Ser. No. 09/549,756 Apr. 14, 2000 now U.S. Pat. No. 6,265,391

This application is a continuation-in-part of U.S. application Ser. No. 09/291,372, filed Apr. 14, 1999, now abandoned, which was a divisional of U.S. application Ser. No. 08/544,330, filed Oct. 17, 1995, now U.S. Pat. No. 5,932,624, issued Aug. 3, 1999, the disclosures of which are hereby incorporated by reference in their entirety.

Homocystinuria is characterized by high serum homocysteine levels and leads to blood vessel damage, excretion of homocysteine in the urine, mental retardation, ectopia lentis, sparse blonde hair, convulsive tendency, thromboembolic episodes, and fatty changes of liver and is associated with defective formation of cystathionine synthetase.

Homocysteine is a homolog of cysteine and is produced by the demethylation of methionine, and is an intermediate in the biosynthesis of cysteine from methionine via cystathionine by cystathioninase.

High serum homocysteine-related blood vessel damage may account for up to 20% of U.S. heart attacks, 40% of strokes and 60% of peripheral venous occlusions, in addition to those in the placenta associated with neural tube defects in about 2,000 infants a year.

It has recently been disclosed that the B vitamins, folic acid and vitamin $B_{12}$, by converting homocysteine to methionine, lower high serum homocysteine and thereby protect against high serum homocysteine-related blood vessel damage and nerve damage. The major sources of folic acid are foods that are often not ingested in sufficient amount, namely fresh fruits and vegetables, particularly the dark green leafy vegetables and orange juice. However, while vitamin $B_{12}$ is in all animal protein, including meat, fish, poultry, eggs, milk and milk products, there is none in anything that grows out of the ground.

Folic acid and vitamin $B_{12}$ are members of the vitamin B complex necessary for the normal production of red blood cells and nerve cells. Folic acid is present in peptide linkages in high quantities in liver, green vegetables and yeast. Vitamin $B_{12}$ is present in high quantities in liver and other animal products.

Many plant and animal tissues contain folic acid as reduced methyl or formyl polyglutamates. Folates act as co-enzymes for processes in which there is transfer of a 1-carbon unit, as in purine and pyrimidine nucleotide biosynthesis, amino acid conversions such as histidine to glutamic acid and generation and use of formate. Absorption takes place in the small intestine. In the gut epithelial cells, polyglutamates are reduced to dihydro- and tetrahydrafolates, and absorbed bound to protein and transported in blood serum as methyl tetrahydrafolate. Some absorbed folate is excreted in the bile and re-absorbed, together with an amount not absorbed and excreted in the stool.

Vitamin $B_{12}$ is necessary for taking a one-carbon unit from folic acid and delivering it to homocysteine to convert homocysteine to methionine. Vitamin $B_{12}$ and folic acid are necessary for normal nerve function as well as for blood formation.

Vitamin Bis involved in a different pathway for getting rid of excess homocysteine, which pathway is usually less important than the $B_{12}$-folate dependent pathway.

Vitamin supplements containing Folic Acid and/or vitamin $B_{12}$ and or Vitamin $B_6$ are known, however, such supplements contain other vitamins, phytochemicals and minerals such as iron and copper, or other antioxidant substances, including antioxidants, which destroy some of Vitamin $B_{12}$ and also some of the folic acid.

In accordance with an aspect of the present invention there is provided a multiple vitamin supplement composition comprising folic acid and vitamin $B_{12}$ that is essentially free of antioxidants.

In accordance with another aspect of the present invention there is provided a multiple vitamin supplement composition comprising folic acid, vitamin $B_{12}$ and vitamin $B_6$ that is essentially free of antioxidants.

In accordance with another aspect of the present invention there is provided a method of administering a multiple vitamin supplement composition for lowering high serum homocysteine levels to protect against the incidence of heart attack and other blood vessel related disorders.

In accordance with another aspect of the present invention there is provided a method of preparing a multiple vitamin supplement composition comprising folic acid and vitamin $B_{12}$ that is essentially free of antioxidants.

In accordance with another aspect of the present invention there is provided a method of preparing a multiple vitamin supplement composition comprising folic acid, vitamin $B_{12}$ and vitamin $B_6$ that is essentially free of antioxidants.

In accordance with the primary aspect of the present invention there is provided a multiple vitamin supplement composition comprising folic acid and vitamin $B_{12}$. The composition may also contain vitamin $B_6$, wherein the composition is essentially free of antioxidants.

It has been shown that folic acid and vitamin $B_{12}$ each have the ability to protect against high serum homocysteine-related blood vessel damage, as in some circumstances, does vitamin $B_6$.

One problem with previous attempts at using vitamin supplements to prevent such cardiovascular problems from developing is that folic acid supplements taken alone are unsafe since they allow unrecognized genetically predisposed vitamin $B_{12}$ deficiency to produce irreversible nerve damage in susceptible populations. Susceptible populations include the elderly (those at least about 50 years of age) and women of African American descent in their child-bearing years.

Accordingly, the multiple vitamin supplement composition of the present invention comprises folic acid and vitamin $B_{12}$, and may also contain vitamin $B_6$. The addition of vitamin $B_{12}$ lowers to normal the vitamin $B_{12}$-deficiency-produced high serum homocysteine found in millions of the elderly.

Vitamin $B_6$, the other B vitamin involved in homocysteine metabolism is also added to the multiple vitamin supplement of the present invention. The addition of vitamin $B_{12}$ and vitamin $B_6$ further metabolizes homocysteine and lowers serum homocysteine levels.

In a preferred embodiment, the multiple vitamin supplement of the present invention contains 400 micrograms of folic acid, 100 micrograms of vitamin $B_{12}$ and 10 milligrams of vitamin $B_6$.

The present invention departs from the prior art in the discovery that the multiple vitamin supplement composition as described above must be essentially free of antioxidants. Antioxidants, including but not limited to other vitamins, minerals such as iron and copper, and other phytochemicals, destroy not only the vitamin $B_{12}$ in the multiple vitamin supplement but also some of the folic acid in the supplement once the vitamin dissolves in the alimentary tract.

By "essentially free" it is meant that the vitamin composition of the present invention must not contain an amount of antioxidants which would tend to damage and inactivate some of the vitamin $B_{12}$ and/or folic acid of the vitamin supplement when dissolved in the digestive tract. The presence of lower amounts of antioxidants would not render the vitamin composition of the present invention ineffective or of reduced effectiveness. Thus, supplemental vitamin C (a biochemically unbalanced synthetic product), which drives free radical formation from iron and heme (Herbert et al, *J. Nutr.*, 126 (suppl. 4):1213S-1220S (1996)) destroys substantial vitamin $B_{12}$ by converting it to useless, or even harmful, analogues. [Herbert, V., in *Present Knowledge in Nutrition* ($7^{th}$ Edition), Washington, D.C. ILSI Press (1996) pp. 191–205]. Free radical generation also destroys substantial folate and gastric intrinsic factor [Shaw et al, *Alcohol*, 7:153–157 (1990)] Further, effective Jan. 1, 1998, the FDA has mandated that all grains also be fortified with 140 μg PGA (pteroylglutamic acid or folic acid) per 100 g grain. Such grains are currently fortified with iron due to an old mandate when negative iron balance was more widespread than the current 6% of all Americans. Also, it has only been learned recently that about 12% of Americans could be harmed by fortifying grains with iron because these persons are heterozygous for hemochromatosis. Many cereals and other products are also fortified with vitamin C.

More recently, based on Framingham data, Jacques et al (*New England J. Medicine,* 340:1449–1454 (1999)) have reported that, while fortification of grains with folic acid (PGA) in elderly adults increased serum folate and decreased serum homocysteine, the difference in mean homocysteine was largely due to differences in vitamin $B_{12}$ and vitamin $B_6$ status between users of B vitamin supplements and non-users. This supports earlier studies that by age 65, about 49% of otherwise healthy elderly adults no longer absorb vitamin $B_{12}$ from food [see: Flynn et al, *J. Am. Coll. Nutr.*, 16:258–267 (1997); Miller et al, *FASEB J.,* 13:A936 (1997); Herbert, *FASEB J.,* 13:A227 (1999)] as determined by low sodium holotranscobalamin II (holo TC II), a surrogate Schilling test, and that about 60% of this 49% had vasculotoxically high (>17) serum homocysteine, and that 100 μg of crystalline vitamin $B_{12}$ orally daily (with malabsorption, 500 μg of vitamin $B_{12}$ intranasally weekly) permanently sustains normal serum total and TCII vitamin $B_{12}$ levels and keeps homocysteine normal. The reason why crystalline vitamin $B_{12}$ and not vitamin $B_{12}$ from food is superior is that, in the natural progression of genetically predisposed gastric atrophy, loss of gastric acid and enzymes precedes loss of intrinsic factor (IF) by years. Thus, without the acids and enzymes, vitamin $B_{12}$ is not split from the proteins in food and is lost in the stool. However, crystalline vitamin $B_{12}$ is free of peptide bonds and is normally absorbed via the physiologic IF-dependent mechanism. With no IF, about 1% of any oral dose of crystalline vitamin $B_{12}$ is absorbed by mass action diffusion. Only 0.1 μg vitamin $B_{12}$ need be absorbed daily to sustain otherwise normal health. Thus, lower mean serum folate in the elderly is large vitamin $B_{12}$ deficiency gut megaloblastosis producing malabsorption of folate, corrected by vitamin $B_{12}$ therapy, and lower red cell folate is secondary both to availability of vitamin $B_{12}$ to transport folate into red cells and to keep it in the red cells by polyglutamating it.

The components of the multiple vitamin supplement of the present invention are co-enzymes which act in accordance with methionine synthetase and cystathioninase and facilitate the production of methionine and cysteine from homocysteine. This lowers the serum level of homocysteine and the high level of heart attacks and other vascular damage and nerve damage associated therewith. The presence of antioxidants in the vitamin composition tends to inactivate the vitamin $B_{12}$ and folic acid components of the vitamin composition once the vitamin composition is processed in the alimentary tract.

Therapeutic treatment with the multiple vitamin supplement of the present invention may involve administration to persons prophylactically, that is to prevent, retard or reduce the severity of future occurrence of the disease or its clinical manifestations.

In accordance with the foregoing, the present invention relates to a process of preventing vitamin $B_{12}$-deficiency induced brain and nervous system damage in a human at least 50 years of age comprising administering to said human a composition comprising at least about 25 μg, or a range of at least about 25 μg to about 1000 μg of vitamin $B_{12}$ wherein said vitamin $B_{12}$ is substantially free of antioxidants. In a specific embodiment, such composition comprises about 100 μg of vitamin $B_{12}$, which could be plus or minus 10 μg.

Among the antioxidants especially to be avoided in such compositions is vitamin C, whether naturally present or added. Obviously, no antioxidants of any kind should be added to any of the compositions disclosed herein (although such antioxidants may be present during the preparation of such vitamins provided that they are removed afterward, either completely or at least to a level where they have virtually no effect on the vitamin components of the present invention). Also to be avoided is the presence of iron (Fe) in such compositions.

In a separate embodiment, the present invention finds especially advantageous use in situations where said human exhibits gastric atrophy.

In accordance with the present invention, the processes disclosed herein are especially useful wherein said brain and nervous system damage comprises brain cell and/or peripheral nerve damage.

Because such antioxidants may be present in vitamin preparations useful in forming the compositions of the present invention, the present invention also relates to processes as already described but wherein said vitamin $B_{12}$ has been tested for the presence of antioxidant and shown to be free of antioxidant. Such testing is commonly performed by liquifying a sample of the product (i.s., the vitamin, or vitamin composition, or vitamin supplement) to be tested in a solution at stomach pH, and another sample at neutral pH, incubating for 30 minutes (the gastric half-emptying time) anf then assaying the amount of vitamin, or vitamins, remaining as compared to the amount prior to incubation.

The present invention also relates to processes such as those described herein where the composition also comprises folic acid in levels disclosed herein.

Pernicious anemia is, in general, a vitamin $B_{12}$ deficiency disease that constitutes a form of homocysteine vasculotoxicity and neurotoxicity.

The present invention further relates to a process of preventing pernicious anemia in a human comprising administering to said human a composition comprising at least about 25 μg, or a range of at least about 25 μg to about 1000 μg of vitamin $B_{12}$ wherein said vitamin $B_{12}$ is substantially free of antioxidants. In a specific embodiment, such composition comprises about 100 μg of vitamin $B_{12}$, which could be plus or minus 10 μg.

Among the antioxidants especially to be avoided in such compositions for preventing pernicious anemia is added vitamin C. Obviously, no antioxidants of any kind should be added to any of the compositions disclosed herein (although such antioxidants may be present during the preparation of such vitamins provided that they are removed afterward, either completely or at least to a level where they have virtually no effect on the vitamin components of the present invention). Also to be avoided is the presence of iron (Fe) in such compositions.

In a separate embodiment, the present invention for preventing pernicious anemia finds especially advantageous use in situations where said human exhibits gastric atrophy. Thus, regardless of whether the vitamin composition, or supplement, or fortificant, of the present invention is to be utilized to prevent pernicious anemia, or peripheral nerve damage, or other condition, 1% of any oral dose of vitamin $B_{12}$ if absorbed by mass action diffusion even after gastric atrophy, which commonly begins in humans as early as age fifty and becomes increasing more prevalent at later ages. In fact, every person between age 50 and age 100 experiences some form of gastric atrophy in a genetically predetermined way. Such atrophy destroys the ability to absorb all of the small doses of vitamin $B_{12}$ (about 1 to 5 $\mu$g) eaten in daily meat, fish, poultry, and other animal products (since there is no vitamin $B_{12}$ in any vegetable matter).

It has also been known for some time that the minimal daily absorbed requirement of vitamin $B_{12}$ to sustain normal health is only about 0.1 $\mu$g. Consequently, even with gastric atrophy and an inability to absorb the vitamin $B_{12}$ in food, a pill containing at least about 25 $\mu$g of vitamin $B_{12}$ daily permits absorption of about 0.25 $\mu$g (1%) ±50% (or 0.125 $\mu$g) thereof, thus guaranteeing sufficient absorbed vitamin $B_{12}$ even though food vitamin $B_{12}$ may be totally unabsorbable.

One problem of gastric atrophy is that as it progresses one loses gastric secretion of enzymes and acid which split vitamin $B_{12}$ from its peptide bonds in food so that no food vitamin $B_{12}$ is absorbed. Thus, the aforementioned 1% absorbability by mass action diffusion applies only to crystalline vitamin $B_{12}$ and not to vitamin $B_{12}$ in food (because the latter is all protein bound). Because of this protein-binding, the compositions disclosed herein should preferably not be taken within an hour (before or after) of eating (since gastric emptying half-time is about 30 minutes).

It is also important to note that the compositions disclosed according to the present invention can be included as supplements or fortificants in foods, such as in breads, cerals, and postas. The levels of vitamin $B_{12}$ disclosed herein should provide no problem with such uses. For example, use of 1000 $\mu$g of vitamin $B_{12}$ in a loaf of bread might tend to cause a pink coloration thereby discouraging sale and consumption whereas use of only 25 $\mu$g to about 500 $\mu$g of vitamin $B_{12}$ in a loaf of bread is sufficient to provide the needed dose but does not cause any unwanted coloration of the bread.

Because antioxidants may be present in vitamin preparations useful in forming the compositions for preventing pernicious anemia, the present invention also relates to processes as already described but wherein said vitamin $B_{12}$ has been tested for the presence of antioxidant and shown to be free of antioxidant.

The compositions useful in the processes of the present invention for preventing pernicious anemia may also comprise folic acid in levels disclosed below. Such compositions may also be in the form of a smart pill.

The multiple vitamin supplement composition of the present invention contains a therapeutically effective amount of folic acid, vitamin $B_{12}$ and may or may not also contain vitamin $B_6$ with the composition being essentially free of antioxidants. The vitamin composition may be administered with a pharmaceutically acceptable carrier. A pharmaceutically acceptable carrier may be any compatible, non-toxic, non-antioxidant substance suitable to deliver the components. The supplement may contain other pharmaceutically acceptable substances as required to approximate physiological conditions such as a pH adjusting and buffering agent, disbursing agents, toxicity adjusting agents, flavoring agents and like. The concentration of the components in these formulations may vary and will be selected primarily on the particular dosage and mode of administration selected. Methods for preparing supplements are well-known or will be apparent to those skilled in the art and are described in more detail in, for example, *Remington's Pharmaceutical Science,* 15th ed., Mack Publishing Company, Easton, Pa.

The supplement is useful for oral administration. The supplement may be formulated in a variety of dosage forms, such as tablets, capsules, oral solutions or suspensions.

Preferably, the supplement is administered orally. For oral administration, solid or fluid dosage forms can be prepared. For preparing solid compositions such as tablets, the components are mixed with conventional ingredients, such as talc, magnesium stearate, and functionally similar materials, as pharmaceutical carriers. Capsules are prepared by mixing the components with an inert pharmaceutical diluent and filling the mixture into a hard gelatin capsule. Soft gelatin capsules are prepared by machine encapsulation of a slurry of the components with an acceptable vegetable oil, light liquid petrolatum or other inert oil. Fluid unit dosage forms for oil administration such as serum and suspensions can be prepared. The components may be dissolved in an aqueous vehicle together with sugar, sweetening and flavoring agents and preservatives to form a serum. Suspensions can be prepared with an aqueous vehicle and a disbursing agent such as acacia, tragacanth, methylcellulose and the like. In accordance with the invention, any carrier, filler or other substance associated with the components of the invention used to prepare a tablet, capsule or the like must be essentially free of anti-oxidants.

In an alternate embodiment of the present invention, separate vitamin compositions may be prepared in accordance with the invention by the methods described above with each containing only Folic acid or Vitamin $B_{12}$. These tablets are essentially free of anti-oxidant substances. In this manner, one or the other component of Folic acid or Vitamin $B_{12}$ can be taken alone such that a user, or their physician, may have more control over the quantity of intake of Folic Acid or Vitamin $B_{12}$, without be forced to also alter the level of intake of the other.

The compositions containing the multiple vitamin supplement components may be administered for the prevention or therapeutic treatment of high serum homocysteine disorders, including prophylactic treatment. In treatment of patients diagnosed with high serum homocysteine levels, the supplement may be administered to a person in an amount sufficient to reduce serum homocysteine levels to normal. In prophylactic treatment, the supplement may be administered to a person who may be at risk of having a high serum homocysteine blood vessel or nerve related disorder, but has not been diagnosed as having such an disorder. An amount adequate to accomplish any of these effects is referred to as a "therapeutically effective" amount. Unit dosages effective for this use will depend upon the severity of the disorder and the general state of the person's health, but will generally range from 25 to about 400 micrograms of folic acid, 25 to about 1,000 micrograms of vitamin $B_{12}$, and 5 to about 20 milligrams of vitamin $B_6$, with 400 micrograms of folic acid, 100 micrograms of vitamin $B_{12}$ and 10 milligrams of vitamin $B_6$ being preferred. The multiple vitamin supplement may be administered in daily dosages and over a period of time with a frequency and duration sufficient to yield a "therapeutically effective" amount, i.e., an amount sufficient to reduce serum homocysteine levels to normal.

What is claimed:

1. A vitamin or supplement composition adapted for administration to a human, the active components thereof consisting essentially of folic acid, 25 to 1000 micrograms vitamin $B_{12}$, and vitamin $B_6$, the composition being essentially free of anti-oxidants.

2. The vitamin or supplement composition of claim 1 wherein the composition is in the form of a capsule.

3. The vitamin or supplement composition of claim 1 wherein the composition is in the form of a tablet.

4. The tablet of claim 3 comprising magnesium stearate.

5. A method of reducing serum homocysteine levels, the method comprising administering a therapeutically effective amount of the composition of claim 4.

6. A method of prophylactic treatment of high serum homocysteine, the method comprising administering a therapeutically effective amount of the composition of claim 1 to a person who may be at risk of having a high serum homocysteine disorder, but has not been diagnosed as having such a disorder.

7. The method of claim 6 wherein the composition is in the form of a tablet.

* * * * *

UNITED STATES PATENT AND TRADEMARK OFFICE
CERTIFICATE OF CORRECTION

PATENT NO. : 6,605,646 B2
DATED : August 12, 2003
INVENTOR(S) : Herbert

It is certified that error appears in the above-identified patent and that said Letters Patent is hereby corrected as shown below:

<u>Title page,</u>
Item [56], References Cited, OTHER PUBLICATIONS,
"Drug Facts and Comparisons" reference, "Fluwer" should be -- Kluwer --.
"Yeland et al.," reference, "19(9)" should be -- 39(9) --.
"Huff et al.," reference, "Huff et all, Physician'" should be -- Huff et al., Physicians' --.
"Stampfer et al.," reference, "Myocaridal" should be -- Myocardial --.
"Brattstrom et al.," reference, "Imparied" should be -- Impaired --.
"Disorders of Red Cells," reference, "Megalolastic" should be -- Megaloblastic --.
"Herbert The Inhibition," reference, "*Birstol-Myers*" should be -- *Bristol-Myers* --.
"V. Herbert 0.4," reference, "Acied" should be -- Acid --.
"V. Herbert," reference, "PLUS CODE 83 IS NOT DEIFNEDg) should be
-- μg --.

<u>Column 1,</u>
Line 4, "which a continuation" should be -- which is a continuation --.
Line 62, "Bis" should be -- $B_6$ is --.

<u>Column 4,</u>
Line 43, "i.s.," should be -- i.e., --.
Line 47, "anf" should be -- and --.

<u>Column 5,</u>
Line 44, "cerals, and postas" should be -- cereals, and pastas --.

UNITED STATES PATENT AND TRADEMARK OFFICE
CERTIFICATE OF CORRECTION

PATENT NO. : 6,605,646 B2
DATED : August 12, 2003
INVENTOR(S) : Herbert

It is certified that error appears in the above-identified patent and that said Letters Patent is hereby corrected as shown below:

Column 6,
Line 47, "without be forced" should be -- without being forced --.
Line 29, "such an disorder" should be -- such a disorder --.

Signed and Sealed this

Thirteenth Day of April, 2004

JON W. DUDAS
*Acting Director of the United States Patent and Trademark Office*